(12) United States Patent
Stever (10) Patent No.: US 10,565,396 B2
(45) Date of Patent: Feb. 18, 2020

(54) PATIENT DATA HUB

(71) Applicant: ZOLL Medical Corporation, Chelmsford, MA (US)

(72) Inventor: Timothy F. Stever, Lowell, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 198 days.

(21) Appl. No.: 15/472,527

(22) Filed: Mar. 29, 2017

(65) Prior Publication Data

US 2017/0300715 A1    Oct. 19, 2017

Related U.S. Application Data

(60) Provisional application No. 62/315,439, filed on Mar. 30, 2016.

(51) Int. Cl.
*G06F 21/62* (2013.01)
*H04L 29/06* (2006.01)
*G16H 10/60* (2018.01)

(52) U.S. Cl.
CPC ......... *G06F 21/6245* (2013.01); *G16H 10/60* (2018.01); *H04L 63/08* (2013.01)

(58) Field of Classification Search
None
See application file for complete search history.

(56) References Cited

U.S. PATENT DOCUMENTS

| | | | |
|---|---|---|---|
| 5,381,798 A | 1/1995 | Burrows | |
| 6,141,584 A | 10/2000 | Rockwell et al. | |
| 6,148,233 A | 11/2000 | Owen et al. | |
| 6,304,780 B1 | 10/2001 | Owen et al. | |
| 6,336,900 B1 | 1/2002 | Alleckson et al. | |
| 6,356,785 B1 | 3/2002 | Snyder et al. | |

(Continued)

FOREIGN PATENT DOCUMENTS

| | | |
|---|---|---|
| EP | 0707825 A2 | 4/1996 |
| JP | 2009-521865 A | 6/2009 |

(Continued)

OTHER PUBLICATIONS

Common Criteria, "Common Criteria for Information Technology Security Evaluation, Part 1—Introduction and General Model", Sep. 2012, 93 pages, Version 3.1, Revision 4.

(Continued)

*Primary Examiner* — Kambiz Zand
*Assistant Examiner* — Arezoo Sherkat
(74) *Attorney, Agent, or Firm* — Finch & Maloney PLLC (57) ABSTRACT

In one example, the patient data hub includes a housing, a first network interface disposed within the housing, a second network interface disposed within the housing, a first controller coupled to the first network interface and a second controller coupled to the second network interface. The first controller is configured to receive sensitive patient data via the first network interface and to transmit the sensitive patient data to the second controller. The second controller is configured to receive the sensitive patient data from the first controller, to secure the sensitive patient data according to a security standard to provide secured sensitive patient data, and to store the secured sensitive patient data in a data storage device.

21 Claims, 7 Drawing Sheets

(56) References Cited

U.S. PATENT DOCUMENTS

| | | |
|---|---|---|
| 6,374,138 B1 | 4/2002 | Owen et al. |
| 6,405,083 B1 | 6/2002 | Rockwell et al. |
| 6,418,346 B1 | 7/2002 | Nelson et al. |
| 6,438,417 B1 | 8/2002 | Rockwell et al. |
| 6,442,433 B1 | 8/2002 | Linberg |
| 6,597,948 B1 | 7/2003 | Rockwell et al. |
| 6,602,191 B2 | 8/2003 | Quy |
| 6,681,003 B2 | 1/2004 | Linder et al. |
| 6,694,191 B2 | 2/2004 | Starkweather et al. |
| 6,920,354 B2 | 7/2005 | Daynes et al. |
| 7,088,233 B2 | 8/2006 | Menard |
| 7,231,258 B2 | 6/2007 | Moore et al. |
| 7,769,465 B2 | 8/2010 | Matos |
| 8,200,195 B2 | 6/2012 | Le Saint et al. |
| 8,287,336 B2 | 10/2012 | Dangler et al. |
| 8,319,632 B1 | 11/2012 | Vaisnys et al. |
| 8,654,749 B2 | 2/2014 | Buchholz et al. |
| 8,768,441 B2 | 7/2014 | De Zwart et al. |
| 9,381,373 B2 | 7/2016 | Geheb et al. |
| 2001/0047140 A1 | 11/2001 | Freeman |
| 2002/0181680 A1 | 12/2002 | Linder et al. |
| 2003/0158593 A1 | 8/2003 | Heilman et al. |
| 2004/0133242 A1 | 7/2004 | Chapman et al. |
| 2005/0216750 A1* | 9/2005 | Bricher ............... G06F 21/602 713/189 |
| 2006/0173498 A1 | 8/2006 | Banville et al. |
| 2007/0233199 A1 | 10/2007 | Moore et al. |
| 2008/0004663 A1 | 1/2008 | Jorgenson |
| 2008/0091175 A1* | 4/2008 | Frikart ............... H04L 63/061 604/891.1 |
| 2008/0097793 A1 | 4/2008 | Dicks et al. |
| 2008/0114406 A1 | 5/2008 | Hampton et al. |
| 2008/0287749 A1 | 11/2008 | Reuter |
| 2009/0005827 A1 | 1/2009 | Weintraub et al. |
| 2009/0058636 A1* | 3/2009 | Gaskill ............. A61N 1/37282 340/539.11 |
| 2009/0073991 A1 | 3/2009 | Landrum et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076350 A1 | 3/2009 | Bly et al. |
| 2009/0146822 A1 | 6/2009 | Soliman |
| 2009/0232286 A1 | 9/2009 | Hurwitz |
| 2010/0241595 A1* | 9/2010 | Felsher ............... G06F 19/328 705/400 |
| 2010/0268304 A1 | 10/2010 | Matos |
| 2010/0324612 A1 | 12/2010 | Matos |
| 2011/0172550 A1 | 7/2011 | Martin et al. |
| 2012/0060030 A1* | 3/2012 | Lamb ............... G06F 21/57 713/166 |
| 2012/0116272 A1 | 5/2012 | Hampton et al. |
| 2012/0191476 A1* | 7/2012 | Reid ............... G06Q 50/24 705/3 |
| 2014/0005736 A1 | 1/2014 | Geheb |
| 2014/0195639 A1 | 7/2014 | Kamen et al. |
| 2014/0337922 A1* | 11/2014 | Sievert ............... A61N 1/37282 726/3 |
| 2015/0058996 A1 | 2/2015 | Maxam et al. |
| 2015/0067769 A1* | 3/2015 | Barton ............... H04W 12/08 726/1 |
| 2015/0149776 A1* | 5/2015 | Chastain ............. H04L 63/0869 713/169 |
| 2016/0110567 A1* | 4/2016 | Rooyakkers ............ G06F 21/86 726/34 |
| 2016/0226865 A1* | 8/2016 | Chen ............... G06F 21/31 |
| 2016/0232010 A1* | 8/2016 | Dicks ............... G06F 8/654 |
| 2017/0075699 A1* | 3/2017 | Narayanan ............ G06F 9/4416 |

FOREIGN PATENT DOCUMENTS

| | | |
|---|---|---|
| JP | 2009-528909 | 8/2009 |
| WO | 1997022297 A1 | 6/1997 |
| WO | 2004078259 A1 | 9/2004 |
| WO | 2011028261 A2 | 3/2011 |
| WO | 2012100219 A1 | 7/2012 |

OTHER PUBLICATIONS

Common Criteria, "Common Criteria for Information Technology Security Evaluation, Part 2—Security Functional Componets", Sep. 2012, 321 pages, Version 3.1, Revision 4.

Common Criteria, "Common Criteria for Information Technology Security Evaluation, Part 3—Security Assurance Components", Sep. 2012, 233 pages, Version 3.1, Revision 4.

Federal Information Processing Standards Publication, "Security Requirements for Cryptographic Modules", May 25, 2001, 69 pages.

Apostol Vassilev, "Annex A: Approved Security Functions for FIPS PUB 140-2, Security Requirements for Cryptographic Modules", Feb. 1, 2016, 8 pages.

Apostol Vassilev, "Annex B: Approved Protection Profiles for FIPS PUB 140-2, Security Requirements for Cryptographic Modules", Nov. 18, 2015, 6 pages.

"Juniper Introduces FIPS—Compliant Operating Systems . . . ", Jul. 18, 2005, 4 pages, <Retrieved online on Feb. 7, 2016>, <URL:http://www.itsecurity.com/security.htm?s=5779>.

Common Criteria, "General-Purpose Operating System Protection Profile", Mar. 6, 2012, 74 pages, version 3.9.

European Search Report for EP Application 13808725.9 dated Jan. 25, 2016, 7 pages.

International Search Report and Written Opinion for PCT Application No. PCT/US2013/047617 dated Nov. 12, 2013.

\* cited by examiner

PATIENT DATA HUB

RELATED APPLICATIONS

This application claims benefit under 35 U.S.C. § 119(e) of U.S. Provisional Application Ser. No. 62/315,439, titled "PATIENT DATA HUB," filed Mar. 30, 2016, which is hereby incorporated herein by reference in its entirety.

BACKGROUND

Doctor's offices, hospitals, and other healthcare organizations deal in sensitive patient information on a daily basis. This sensitive patient information may include, for example, information descriptive of treatment a patient has undergone, payment the patient has made for treatment, and the patient's past, present, and predicted future health. Given the importance and private nature of sensitive patient information, healthcare organizations implement a variety of security measures to both share and protect it. These security measures include both physical security measures and cybersecurity measures. Physical security measures restrict physical access to sensitive patient information and equipment dealing therewith. For example, physical security measures may include file cabinet locks, door locks, and security systems. Cybersecurity measures restrict access to digitized sensitive patient information and equipment dealing therewith. Cybersecurity measures include encrypting sensitive patient information and requiring entry and verification of authentication credentials prior to granting a user access to a computer system or network in which sensitive patient information is stored.

The physical security measures and cybersecurity measures employed by healthcare organizations may meet the requirements of any of a variety of information security standards. Examples of these standards include, for example, ISO/IEC 15408 as defined the International Organization for Standardization (ISO), standards defined by regulations promulgated under the Health Insurance Portability and Accountability Act of 1996 (HIPAA), and standards defined by regulations promulgated under the Federal Information Security Management Act of 2002 (FISMA). For instance, FISMA provides the legal basis for certain federal government facilities, such as Veteran's Administration hospitals, to require that equipment processing sensitive patient information be compliant with the Federal Information Processing Standard (FIPS). To be certified FIPS compliant, equipment that processes sensitive patient information must undergo a rigorous process that ensures the equipment meets the requirements of at least one of four security levels defined by the FIPS.

SUMMARY

In accordance with some examples of the present disclosure, a patient data hub is provided. In some examples, the patient data hub isolates information processing devices that are compliant with one or more security standards from other information processing devices that may or may not be compliant with the one or more security standards. For instance, one example is directed to a patient data hub that receives information from medical devices that are not compliant with FIPS, processes the information, and makes the information accessible to FIPS compliant devices in a secure manner that does not compromise the compliant devices' FIPS certification. Thus, in this example, the patient data hub acts as an intermediary between FIPS compliant devices connected to a network of a healthcare organization and other devices that are not FIPS compliant. Further, the introduction of the patient data hub into this environment enables the non-compliant devices to remain non-compliant while providing sensitive patient data to the compliant devices.

In one example, a patient data hub includes a housing, a first network interface disposed within the housing, a second network interface disposed within the housing, a first controller coupled to the first network interface and a second controller coupled to the second network interface. The first controller is configured to receive sensitive patient data via the first network interface and to transmit the sensitive patient data to the second controller. The second controller is configured to receive the sensitive patient data from the first controller, to secure the sensitive patient data according to a security standard to provide secured sensitive patient data, and to store the secured sensitive patient data in a data storage device.

The patient data hub may further include a tamper-evident device that protects the second controller and the second controller may be configured to authenticate an operator within a role prior to allowing the operator to execute any of a plurality of services associated with the role. The tamper-evident device may include at least one of a coat and a seal.

The patient data hub may further include an isolated interface and a security device protecting the second controller. The security device may be configured to zeroize critical security parameters in response detecting tampering. The second controller may be configured to authenticate an operator's identity prior to allowing the operator to execute any of a plurality of services associated with the operator and allow external access to plaintext critical security parameters only through the isolated interface. The security device may surround the second controller. The second controller may be configured to zeroize all critical security parameters in response to detecting transgression of one or more threshold values by one or more environmental conditions. The one or more environmental conditions may include current supplied to the second controller and a temperature of the second controller.

The patient data hub may further include the data storage device and the security device may surround the data storage device. In the patient data hub, the sensitive patient data may be encoded in a self-descriptive, extensible data format. The security standard may include at least one of encryption and compression. The security standard may be compliant with at least one Federal Information Processing Standard security level.

In the patient data hub, the first controller may be configured to synchronize chronological data elements of the sensitive patient data with reference to a time identified by the first controller. The second controller may be configured to receive configuration information, store the configuration information, and transmit the configuration information to the first controller. The configuration information may include information descriptive of at least one of a new device model, a new data type, and a new security function.

In one example, a system is provided. The system includes a patient data hub. The patient data hub includes a housing, a first network interface disposed within the housing, a second network interface disposed within the housing, a first controller coupled to the first network interface, and a second controller coupled to the second network interface. The first controller is configured to receive sensitive patient data via the first network interface and to transmit the sensitive patient data to the second controller. The second controller is configured to receive the sensitive patient data from the first controller, to secure the sensitive patient data according to a security standard to provide secured sensitive patient data, and to store the secured sensitive patient data in a data storage device. The system also includes at least one medical device coupled to the first network interface and a hospital information system coupled to the second network interface.

In the system, the sensitive patient data may be encoded in a self-descriptive, extensible data format. The security standard may be compliant with at least one Federal Information Processing Standard security level. The first controller may be configured to synchronize chronological data elements of the sensitive patient data with reference to a time identified by the first controller. The second controller may be configured to receive configuration information, store the configuration information, and transmit the configuration information to the first controller. The configuration information may include information descriptive of at least one of a new device model, a new data type, and a new security function.

In one example, a patient data module is provided. The patient data module comprises a substrate, a first network interface disposed upon the substrate, a second network interface disposed upon the substrate, a first controller coupled to the first network interface, and a second controller coupled to the second network interface. The first controller is configured to receive sensitive patient data via the first network interface and to transmit the sensitive patient data to the second controller. The second controller is configured to receive the sensitive patient data from the first controller, to secure the sensitive patient data according to a security standard to provide secured sensitive patient data, and to store the secured sensitive patient data in a data storage device. The patient data module may be configured to be coupled to a medical device.

In the patient data module, the sensitive patient data may be encoded in a self-descriptive, extensible data format. The security standard may be compliant with at least one Federal Information Processing Standard security level. The first controller may be configured to synchronize chronological data elements of the sensitive patient data with reference to a time identified by the first controller. The second controller may be configured to receive configuration information, store the configuration information, and transmit the configuration information to the first controller. The configuration information may include information descriptive of at least one of a new device model, a new data type, and a new security function.

In one example, a method of storing sensitive patient data acquired by a medical device using a patient data hub is provided. The patient data hub includes a controller and a cryptographic component. The method includes acts of receiving, by the controller, the sensitive patient data from the medical device; identifying, by the controller, an operator of the medical device; authenticating, by the cryptographic component, the operator to a role authorized to secure data; securing in accordance with a security standard, by the cryptographic component, the sensitive patient data to provide secured sensitive patient data in response to authenticating the operator to the role; and storing, by the cryptographic component, the secured sensitive patient data.

In the method, the act of securing the sensitive patient data may include an act of securing the sensitive patient data using a security standard that is compliant with at least one Federal Information Processing Standard security level. The method may further comprise an act of synchronizing chronological data elements of the sensitive patient data with reference to a time identified by the controller. The method may further comprise an act of receiving configuration information, storing the configuration information, and transmitting the configuration information to the controller. The act of receiving the configuration information may include an act of receiving information descriptive of at least one of a new device model, a new data type, and a new security function.

Still other aspects, examples and advantages of these aspects and examples, are discussed in detail below. Moreover, it is to be understood that both the foregoing information and the following detailed description are merely illustrative examples of various aspects and features, and are intended to provide an overview or framework for understanding the nature and character of the claimed aspects and examples. Any example or feature disclosed herein may be combined with any other example or feature. References to different examples are not necessarily mutually exclusive and are intended to indicate that a particular feature, structure, or characteristic described in connection with the example may be included in at least one example. The appearances of such terms herein are not necessarily all referring to the same example.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects, and are incorporated in and constitute a part of this specification, but are not intended as a definition of the limits of any particular example. The drawings, together with the remainder of the specification, serve to explain principles and operations of the described and claimed aspects. In the figures, each identical or nearly identical component that is illustrated in various figures is represented by a like numeral. For purposes of clarity, not every component may be labeled in every figure.

DETAILED DESCRIPTION

Various examples described herein are directed to a patient data hub that is configured to receive sensitive patient data, store the sensitive patient data in a manner that complies with one or more security standards, and make the secured sensitive patient data available to trusted devices.

These trusted devices may include computer systems certified as being compliant with the one or more security standards and operated by authenticated healthcare personnel. In some examples, the patient data hub is configured to receive the sensitive patient data from devices (e.g., medical devices) that may or may not comply with the one or more security standards. By being configured in this manner, the patient data hub is positioned to act as an intermediary between certified devices that comply with the one or more security standards and uncertified devices that do not. Thus at least some examples of the patient data hub allow certified devices to receive and leverage sensitive patient data from uncertified devices without compromising security and without requiring that the uncertified devices undergo certification.

As summarized above, one example of the patient data hub connects uncertified and potentially uncompliant devices with devices certified to be compliant with the standard defined by FIPS PUB 140-2, which is hereby incorporated herein by reference in its entirety. In broad overview, FIPS 140-2 provides for four levels of increasing security. FIPS level 1 provides the lowest level of security and requires a cryptographic component that encrypts data using an approved process or security function.

FIPS level 2 includes the requirements of level 1 and additionally requires physical security mechanisms that include a tampering indicator for the cryptographic component or pick-resistant lock on removable elements that provide access to the cryptographic component. In addition, level 2 requires at least role-based authentication of an operator to perform any cryptographic services associated with the role. Level 2 also requires, where the cryptographic module is executed on a general purpose computing system, that an operating system of the general purpose computing system meet the functional requirements specified in the Common Criteria Protection Profiles listed in Annex B of the FIPS 140-2 standard and be evaluated to at least the Common Criteria evaluation assurance level of EAL2.

FIPS level 3 includes the requirements of level 2 and additionally requires components configured to erase "critical security parameters" (CSPs), e.g., keys, passwords, etc., used to access encrypted data in response to detecting any unauthorized attempt at physical access, use, or modification of the cryptographic component. In addition, level 3 requires at least identity-based authentication of an operator to perform any cryptographic services associated with the operator's role. Furthermore, level 3 requires that plaintext CSPs be input or output via a physically separated port or logically separated interface using a Trusted Path (e.g., a communication channel facilitated via transport layer security (TLS)). Level 3 also requires, where the cryptographic module is executed on a general purpose computing system, that the operating system of the general purpose computing system meet the functional requirements specified in the Common Criteria Protection Profiles listed in Annex B of the FIPS 140-2 standard, support the functional requirement of a Trusted Path, and be evaluated to at least the Common Criteria evaluation assurance level of EAL3 with the additional assurance requirement of an Informal Target of Evaluation (TOE) Security Policy Model.

FIPS level 4 includes the requirements of level 3 and additionally requires a complete envelope of protection around the cryptographic component that detects and responds to all unauthorized attempts at physical access. Responses to attempts at physical access or tampering must include erasure of CSPs. In addition, level 4 requires components configured to thwart indirect attempts at tampering with the cryptographic component, such as by manipulation of the environment of the cryptographic component (e.g. via temperature or electrical variance). These components may detect such indirect tampering and respond by erasing CSPs or may protect the cryptographic component from such indirect tampering via one or more protective measures. Level 4 also requires, where the cryptographic module is executed on a general purpose computing system, that the operating system of the general purpose computing system meet the requirements of level 3 and be evaluated to at least the Common Criteria evaluation assurance level of EAL4.

As described in detail further below, various examples disclosed herein provide for patient data hubs that connect devices that comply with each security level defined by FIPS.

Examples of the methods and systems discussed herein are not limited in application to the details of construction and the arrangement of components set forth in the following description or illustrated in the accompanying drawings. The methods and systems are capable of implementation in other examples and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, components, elements or acts of the systems and methods herein referred to in the singular may also embrace examples including a plurality, and any references in plural to any example, component, element or act herein may also embrace examples including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

System Overview

Figure 1:
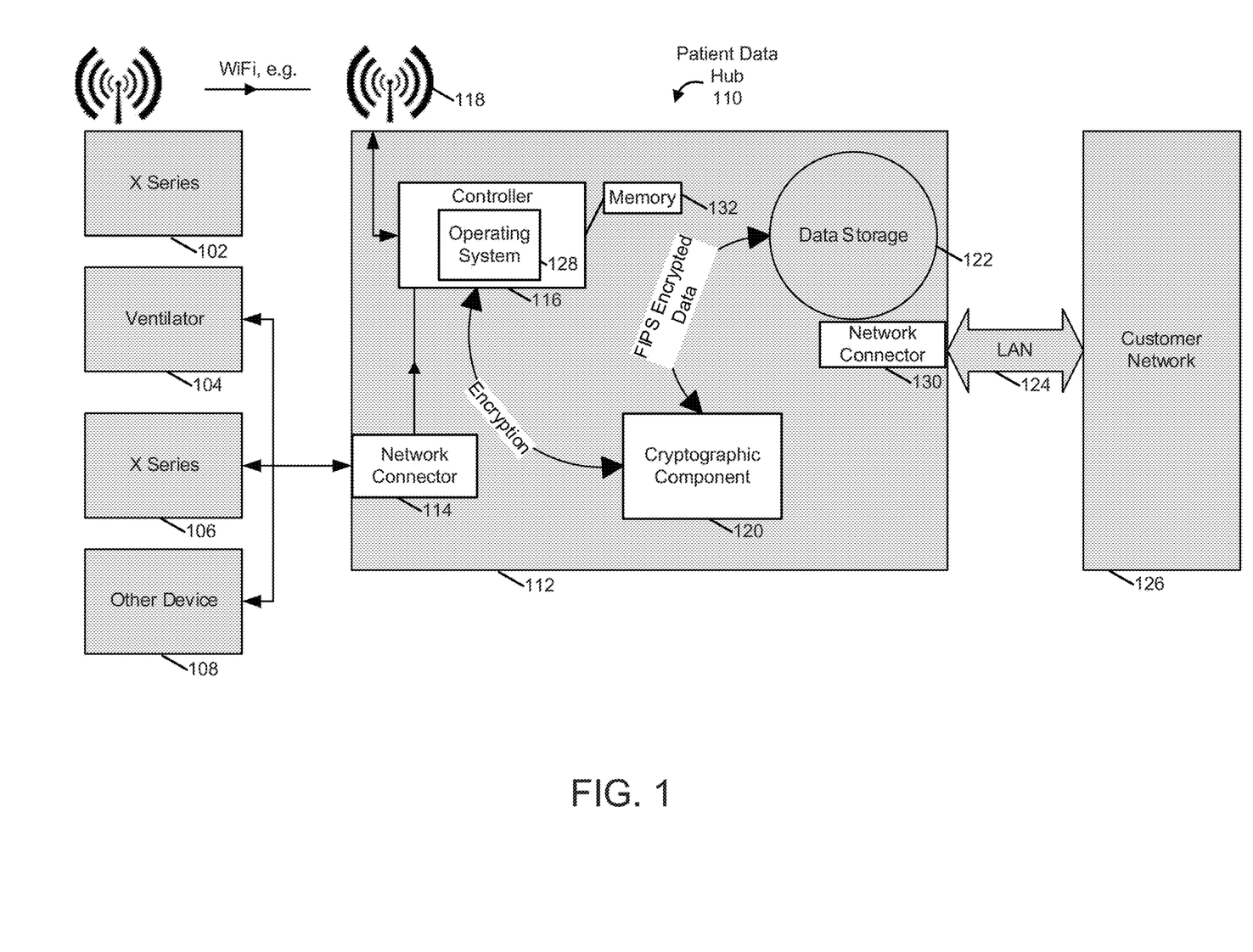
FIG. 1 is a block diagram illustrating a patient data hub within a hospital environment in accordance with an example of the present disclosure.

In some examples, a patient data hub acts as an protective device that shields portions of a hospital's information technology infrastructure from devices that do not comply with the hospital's security standards, while allowing those devices to contribute data toward patient care. FIG. 1 is a context diagram that illustrates such a patient data hub 110 within a hospital environment in accordance with at least one example. As shown, FIG. 1 includes defibrillators 102 and 106, ventilator 104, other devices 108, the patient data hub 110, a local area network (LAN) 124, and a customer network 126. Each of the defibrillators 102 and 106 may be any of a variety of commercially available defibrillators, such as an X Series® brand defibrillator available from ZOLL® Medical Corporation of Chelmsford, Mass. The ventilator 104 may be any of a variety of commercially available ventilators, such as an EMV+™ brand ventilator available from ZOLL® Medical Corporation. The other devices 108 may be any of a variety of medical devices, such as other defibrillators (including wearable defibrillators such as a LifeVest® brand wearable defibrillator available from ZOLL® Medical Corporation), ventilators, resuscitators, and temperature management systems, or non-medical devices that carry sensitive patient data or, in some examples, other information. The LAN 124 may include a variety of network forwarding devices, such as hubs, routers, and switches. The customer network 126 may include a hospital information system (HIS) that is isolated and secure from external access.

As illustrated in FIG. 1, the patient data hub 110 is configured to receive sensitive patient data from the devices 102, 104, 106, and 108, process the inbound data, store the inbound data, and make the inbound data available to trusted devices within the customer network 126 via the LAN 124. In some examples in accordance with FIG. 1, the patient data hub 110 is fabricated from production grade materials and includes a housing 112, network connectors 114 and 130, a controller 116, memory 132, a wireless antenna 118, a cryptographic component 120, and patient data storage 122. In these examples, the housing 112 is configured to securely hold the other components of the patient data hub 110 and may be formed of any of various materials including, for example, aluminum, injection molded plastics, and production grade housing materials. The network connector 114 may include any of a variety of connectors such as serial connectors, parallel connectors, USB connectors, RJ45 connectors, and the like. The wireless antenna 118 may include any of a variety of antennas such as cellular, Wi-Fi, or other antennas. In some examples, other data transmission mechanisms may be used in place of or in addition to the wireless antenna 118. Examples of these other data transmission mechanisms include transceivers that communicate via optics, acoustics, and inductive coupling. The network connector 130 may include any of the aforementioned wired and/or wireless connectors. The patient data storage 122 may include any of a variety of nonvolatile and/or volatile memory, such as flash memory or magnetic disk.

The memory 132 may include any of a variety of computer readable and/or writable memory, such as CMOS, RAM, ROM, flash memory, and the like. In some examples, the memory 132 is configured to store software defining an operating system 128, which controls the operation of components of the patient data hub 110. Alternatively or additionally, the memory 132 may be configured to store software defining processes described below with reference to FIGS. 6 and 7.

To support execution of processes that secure and filter inbound data, which are described in further detail below, the memory 132 may also be configured to store configuration information descriptive of data elements the cryptographic component 120 is configured to receive and process from external devices. For example, this configuration information may be stored in the form of a lookup table including fields configured to store identifiers of authorized data element types (e.g., electrocardiogram (ECG) data, patient temperature data, etc.) and fields configured to store identifiers of device types (e.g., device manufacturer and model) as illustrated in Table 1.

TABLE 1

| Device Type | Data Element Type |
|---|---|
| X Series ® Defibrillator | ECG data |
| Ventilator | Respiration data |
| LifeVest ® Defibrillator | Location data |

The controller 116 may include one or more of a variety of processors or controllers such as a multi-core processor, single-core processor, or microcontroller. The controller 116 is configured to perform a series of instructions that result in manipulated data. The controller 116, by being coupled to the memory 132 and the software stored therein, is configured to implement the operating system 128 and other processes described herein.

As shown in FIG. 1, the controller 116 is coupled to the network connector 114, the wireless antenna 118, the memory 132, and the cryptographic component 120. The controller 116 is configured to exchange inbound data (e.g., the sensitive patient data) with the defibrillator 102 via the wireless antenna 118. Similarly, the controller 116 is configured to exchange inbound data with the ventilator 104, the defibrillator 106, and the other devices 108 via the network connector 114.

In some examples, the controller 116 is configure to execute a communication component as disclosed in U.S. Patent Application Publication No. 2016/0321400, titled CLINICAL DATA HANDOFF IN DEVICE MANAGEMENT AND DATA SHARING, published Nov. 3, 2016, which is hereby incorporated herein by reference in its entirety. Such a communication component may facilitate communication between a first medical device and a second medical device during a medical event. This communication may include transfer, display, and operational use of clinical information collected by the first medical device.

In some examples, the controller 116 is configured to receive, parse, filter, augment, and otherwise process the inbound data prior to transmitting the inbound data to the cryptographic component 120. For instance, the controller 116 may be configured to reorganize the inbound data into a self-descriptive, extensible format (e.g., XML, JSON, etc.), compress, and/or encrypt the inbound data prior to transmitting the inbound data to the cryptographic component 120 within a request for cryptographic services and storage. Examples of receiving, parsing, filtering, augmenting, and other processes the controller 116 is configured to execute prior to transmitting the inbound data to the cryptographic component 120 are described further below with reference to FIG. 7.

The inbound data received and processed by the controller 116 may encode a wide variety of information. Examples of this information include patient demographic data (e.g., name, address, insurance provider, etc.), patient physiological information (e.g., ECG data, body temperature, etc.), information descriptive of healthcare provider observations of the patient, images of the patient, device information (e.g., manufacturer, model, operational status, remaining battery power, etc.), environmental information (e.g., ambient temperature, noise level, device location, etc.), and identifiers of device operators.

In some examples, the controller 116 is also configured to receive and process configuration information, such as the configuration described above with reference to Table 1. Examples of configuration processes that the controller 116 is configured to execute are described further below with reference to FIG. 6.

The cryptographic component 120 may include any of a variety of controllers and, in some examples, is configured to provide cryptographic services (e.g., compression, encryption, etc.) in response to requests received from the controller 116. As shown, the cryptographic component 120 is coupled to and configured to communicate with the controller 116 and the data storage 122.

In some examples, the cryptographic component 120 is configured to receive, process, and store configuration information received from an input, such as the data port 202 described below with reference to FIG. 2. This configuration information may include CSPs, information descriptive of data elements the cryptographic component is configured to receive from the controller 116, and information descriptive of relationships between identifiers of operators, roles, and cryptographic services that the roles are authorized to execute. Examples of configuration processes that the cryptographic component 120 is configured to execute are described further below with reference to FIG. 6.

In some examples, the cryptographic component 120 is configured to process inbound data received from the controller 116 into a format that complies with one of the security levels of FIPS and store the inbound data in the data storage 122. In this way, trusted devices connected to the customer network 126 may access the inbound data stored on the data storage 122 via the LAN 124 and the network connector 130 according to FIPS requirements. Examples of reformatting and storage processes that the cryptographic component 120 is configured to execute are described further below with reference to FIG. 7.

Figure 2:
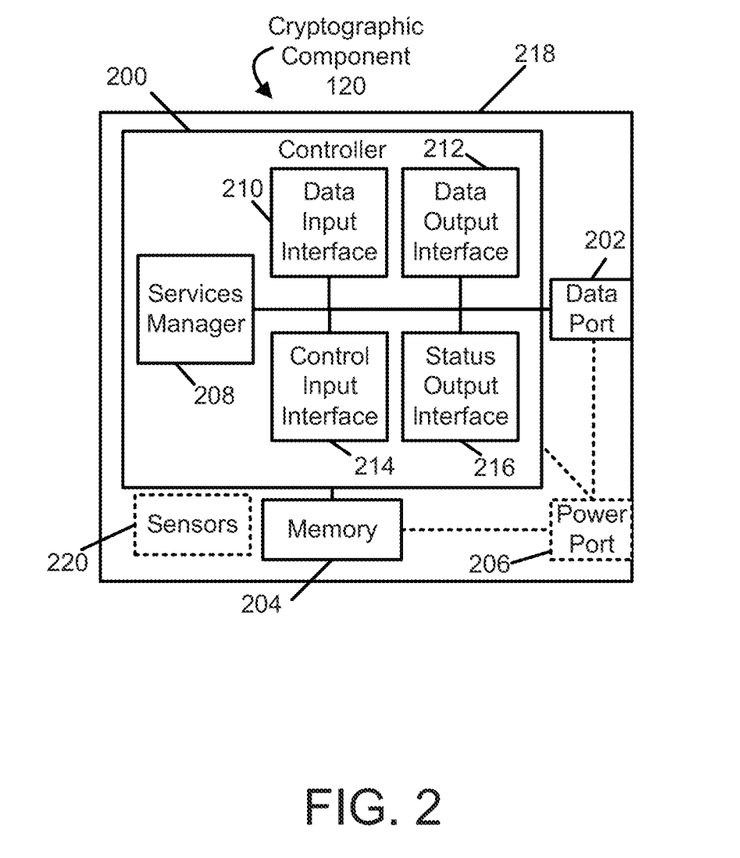
FIG. 2 is a block diagram illustrating components of a cryptographic component illustrated in FIG. 1 in accordance with an example of the present disclosure.

FIG. 2 illustrates the cryptographic component 120 in more detail. As shown, the cryptographic component 120 includes a housing 218, a controller 200 coupled to a data port 202, a memory 204, a power port 206, and a sensor 220. The controller 200 is configured to implement a services manager 208, a data input interface 210, a data output interface 212, a control input interface 214, and a status output interface 216.

In some examples, the housing 218 is formed from materials that are rigid and opaque, such as production grade plastics or metals. As shown in FIG. 2, the housing 218 physically contains all of the components of the cryptographic component 120. The housing 218 may include tamper indicators, for example pick resistant locks and/or is sealed or coated with a material that indicates any attempts to tamper with the cryptographic component 120. For instance, the housing 218 may be secured to a substrate by rivets or other fasteners that may not be removed and refastened or may be covered by a label that may not be removed and reapplied. In some examples, the housing 218 surrounds the other components of the cryptographic component 120 and provides them with a complete envelope of protection.

In some examples of tamper indicators, the housing 218 includes one or more sensors 220 capable of detecting data indicative of tampering. The one or more sensors 220 may include light sensors (e.g., photoelectric sensors), motion sensors (e.g., accelerometers, gyroscopes, magnetometers, or other inertial measurement units), temperature sensors, electrical conduction sensors, and electrical capacitance sensors, among other types of sensor. As is described further below, in some examples the services manager 208 is configured to execute services that use data acquired by the one or more sensors to detect attempts to tamper with and/or gain physical access to components within the housing 218.

The data port 202 may include any of a variety of interconnection mechanisms, such as a serial or parallel bus. In some examples, the data port 202 includes a plurality of data ports. The power port 206 is optional and may be replaced by a power source (e.g. a battery, energy harvesting device, etc.) contained within the housing 218. The sensor 220 is optional and described further below. The memory 204 may include any of a variety of computer readable and/or writable memory, such as CMOS, RAM, ROM, flash memory, and the like. For example, in some instances, the data storage 122 is disposed within the memory 204. The memory 204 may be configured to store, in addition to the data described below with reference to the interfaces 210, 212, 214, and 216, software defining the services manager 208 and the interfaces 210, 212, 214, and 216. The controller 200, by being coupled to the memory 204 and the software stored therein, is configured to implement the services manager 208 and the interfaces 210, 212, 214, and 216. The memory 204 may also store configuration information as described above.

In some examples, the data input interface 210 is configured to receive all input data addressed to the cryptographic component 120 except for control data received via the control input interface 214. Examples of this input data include configuration information, plaintext data, cipher text data, cryptographic keys and CSPs, authentication data, and status information from other components. The control input interface 214 is configured to receive all control data addressed to the cryptographic component 120. Examples of this control data include service requests that control the operation of the cryptographic component. The data output interface 212 is configured to transmit all output data addressed to external devices except for status data. Examples of this output data include configuration information, plaintext data, cipher text data, cryptographic keys and CSPs, authentication data, and control information from other components. The status output interface 216 is configured to transmit status data to external devices. Examples of this status data include return codes and signals that activate or deactivate physical indicators, such as the light emitting diode 304 describe further below with reference to FIG. 3.

In the example illustrated in FIG. 2, each of the interfaces 210, 212, 214, and 216 is configured to communicate with external devices via the data port 202. As shown, the input interfaces 210 and 214 are each configured to communicate with external devices via the data port 202. Similarly, the output interfaces 212 and 214 are each configured to communicate with external devices via the data port 202. In some examples, for additional security, both of the input interfaces 210 and 214 are individually configured to determine whether either of the output interfaces 212 and 216 is active and, if so, to not communicate via the data port 202. Also for additional security, in some examples, both of the output interfaces 212 and 216 are individually configured to determine whether either of the input interfaces 210 and 214 is active and, if so, to not communicate via the data port 202. Input or output exclusivity may be managed, for example, via the use of a common semaphore, mutex, or other access management data structure.

In some examples, the data port 202 includes a plurality of data ports in which one data port is isolated from other data ports. In these examples, the input interfaces 210 and 214 use the isolated data port and the output interfaces 212 and 216 use another data port. In at least one example, the data input interface 210 is configured to receive manually entered plaintext keys and other CSPs via the isolated data port.

In some examples, the services manager 208 is configured to determine whether either of the output interfaces 212 and 216 is active and, if so, to not execute services that generate keys, receive manually entered keys, or erase (e.g., zeroize) keys. Further, in some examples, the services manager 208 is configured to prevent inadvertent output of sensitive information by transmitting plaintext keys or CSPs only after two distinct physical or logical actions have been performed. For example, prior to transmitting plaintext keys or CSPs, the services manager 208 may require that two discrete physical switches be actuated, a single physical switch be actuated two or more times within a predetermined period of time, two distinct electronic signals be received via an input (e.g., the data port), or the like.

In some examples illustrated by FIG. 2, the services manager 208 is configured to execute a variety of operations. These operations include outputting a current status of the cryptographic component 120, executing one or more self-tests (e.g., cryptographic process tests, software integrity tests, and critical function tests), and executing a security function approved for use by the current operator in the current mode of operation. Examples of approved security functions include transition functions, symmetric key functions, asymmetric key functions, message authentication functions, and hashing functions. The symmetric and asymmetric key functions may include key generation functions, key establishment functions, key entry and output functions, key storage functions, and key zeroization functions. In at least some examples, the approved security functions comply with those described within Annex B of the FIPS 140-2 standard. In some examples, the services manager 208 is configured to compress, encrypt, or otherwise secure sensitive patient data to generate secured sensitive patient data. This secured sensitive patient data may be transmitted via the data output interface 212 for storage in the data storage 122.

In some examples, the service manager 208 is also configured to execute an authentication service. In at least one example, the authentication service is configured to authenticate an operator to a role (e.g., via credentials associated with the role). In another example, the authentication service is configured to first authenticate the identity of the operator (e.g., via credentials associated with the individual) and then to authenticate the operator to a role using information associating the individual with the role. In both of these examples, the authentication service is configured to determine whether a role is authorized to execute one or more of the service manager operations described above.

In some examples, the services manager 208 is configured to execute a monitoring service that monitors the sensor 220 and zeroizes all plaintext secret and private cryptographic keys and CSPs upon detection of an attempt to tamper with and/or gain physical access to any of the components of the cryptographic component 120. For instance, in some examples, the sensor 220 includes a temperature sensor (e.g., a thermometer) configured to measure the temperature of the environment inside the housing 218. In these examples, the services manager 208 is configured to execute a service that monitors temperature measurements acquired by the temperature sensor and zeroizes all plaintext secret and private cryptographic keys and CSPs in response to detecting a temperature that exceeds a threshold value.

In some examples, to increase the overall security provided, the service manager 208 selective shields particular data elements by incorporating and executing a shielding component that is configured in accordance with the shielding component disclosed in U.S. Patent Application Publication No. 2016/0321418, titled CUSTOMER- OR PATIENT-BASED SELECTIVE DATA ENCRYPTION IN MEDICAL DEVICE MANAGEMENT, published Nov. 3, 2016, which is hereby incorporated herein by reference in its entirety.

In some examples, the sensor 220 includes a power sensor (e.g., an ammeter) is configured to that measure the level of power being supplied to the cryptographic component via, for example, the power port 206. In these examples, the services manager 208 is configured to execute a service that monitors current measurements acquired by the power sensor and zeroizes all plaintext secret and private cryptographic keys and CSPs in response to detecting a current that exceeds a threshold value.

In some examples, the sensor 220 includes a light sensor (e.g. a photoelectric cell) that is configured to measure radiant flux of the environment within the housing 218. In these examples, the services manager 208 is configured to execute a service that monitors radiant flux measurements acquired by the light sensor and zeroizes all plaintext secret and private cryptographic keys and CSPs in response to detecting a radiant flux that exceeds a threshold value.

In some examples, the sensor 220 includes an audio sensor (e.g. a microphone) that is configured to measure the sound level of the environment within the housing 218. In these examples, the services manager 208 is configured to execute a service that monitors sound measurements acquired by the audio sensor and zeroizes all plaintext secret and private cryptographic keys and CSPs in response to detecting a radiant flux that exceeds a threshold value.

In some examples, the sensor 220 includes an audio sensor that is configured to measure the frequency of the sounds within the environment within the housing 218. In these examples, the services manager 208 is configured to execute a service that monitors frequency measurements acquired by the audio sensor and zeroizes all plaintext secret and private cryptographic keys and CSPs in response to detecting a change in frequency that exceeds a threshold value.

In some examples, the sensor 220 includes a capacitance sensor that is configured to measure capacitance of the housing 218. In these examples, the services manager 208 is configured to execute a service that monitors capacitance measurements acquired by the capacitance sensor and zeroizes all plaintext secret and private cryptographic keys and CSPs in response to detecting a change in capacitance that exceeds a threshold value.

In some examples, the sensor 220 includes a conduction sensor that is configured to measure conductance of one or more circuits formed the housing 218. In these examples, the services manager 208 is configured to execute a service that monitors conductance measurements acquired by the conductance sensor and zeroizes all plaintext secret and private cryptographic keys and CSPs in response to detecting a change in conductance that exceeds a threshold value.

In some examples, the sensor 220 includes a motion sensor (e.g., accelerometers) that is configured to measure the motion of the housing 218. In these examples, the services manager 208 is configured to execute a service that monitors motion measurements acquired by the motion sensor and zeroizes all plaintext secret and private cryptographic keys and CSPs in response to detecting a motion that exceeds a threshold value.

In some examples, the sensor 220 includes two motion sensors that are configured to measure the motion of the housing 218 and a controller 200. In these examples, the services manager 208 is configured to execute a service that monitors motion measurements acquired by the motion sensors and zeroizes all plaintext secret and private cryptographic keys and CSPs in response to detecting a difference in relative motion that exceeds a threshold value.

In some examples, the services manager 208 is configured to execute a heartbeat service that periodically (e.g. every millisecond) exchanges heartbeat transmissions with the controller 116. Heartbeat transmissions may be used to indicate the device transmitting the heartbeat remains operational. Heartbeat transmissions may be unidirectional, bidirectional, and initiated or received by either the services manager 208 or the controller 116. In these examples, the service monitors heartbeat transmissions and zeroizes all plaintext secret and private cryptographic keys and CSPs in response to detecting a number of missed heartbeats (e.g., heartbeats that are not received within a predetermined time window) that exceed a threshold value (e.g., 2-5).

In some examples, any of the monitoring services described above may be temporarily terminated by an operator with sufficient authority to enable maintenance to be performed on the patient data hub. Further, in some examples, the operating system 128 is configured to provide a trusted path via the network connector 114 to the data port 202, and the data input interface 210 for plaintext cryptographic key components, authentication data, and CSPs. A trusted path is a communication session in which both the identity of the sender and the identity of the receiver of the communication are verified (e.g., via credentials, certificates, etc.) and the individual communications are secure (e.g., via encryption). Trusted path may be used to transmit configuration information to the patient data hub and/or perform other maintenance on the patient data hub.

Additional Examples

Figure 3:
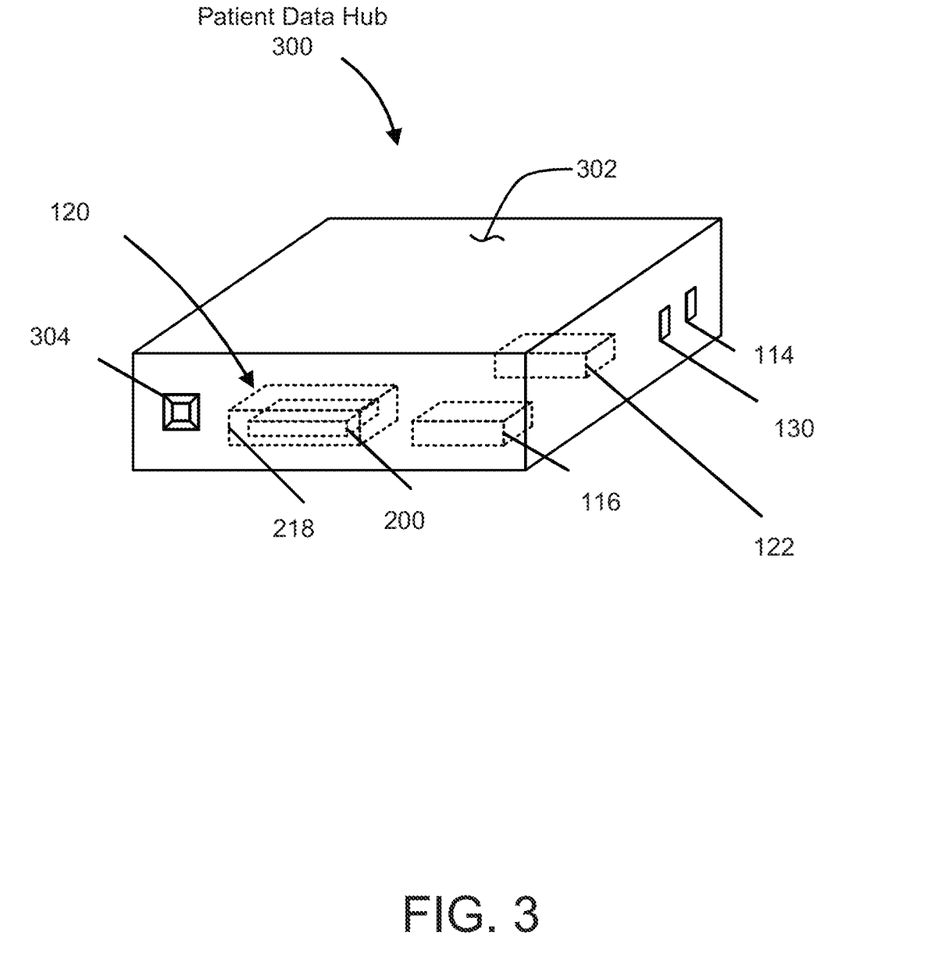
FIG. 3 is a block diagram illustrating another patient data hub in accordance with an example of the present disclosure.

FIG. 3 illustrates another example of a patient data hub 300 that includes various components previously described. As shown, the patient data module 300 includes a visual indicator 304, network connectors 114 and 130, the controller 116, the cryptographic component 120, and the data storage 122. The cryptographic component 120 includes the housing 218, the controller 200, and other components (not shown) of the cryptographic component 120. In addition, the patient data hub 300 includes a housing 302 and a visual indicator 304 (e.g., a light emitting diode). As shown, the visual indicator 302 is integrated with the housing 302. In this example, the patient data hub 300 is configured to indicate a tampering attempt by illuminating the visual indicator 304. In some examples, a switch (not shown) disposed within the housing 302 is coupled to a power source (not shown), and the switch is configured to couple the power source to the visual indicator 304 to supply power to the visual indicator 304 in response to receiving a control signal that indicates tampering from the cryptographic component 120 via the status output interface 216 and the data port 202.

Figure 4:
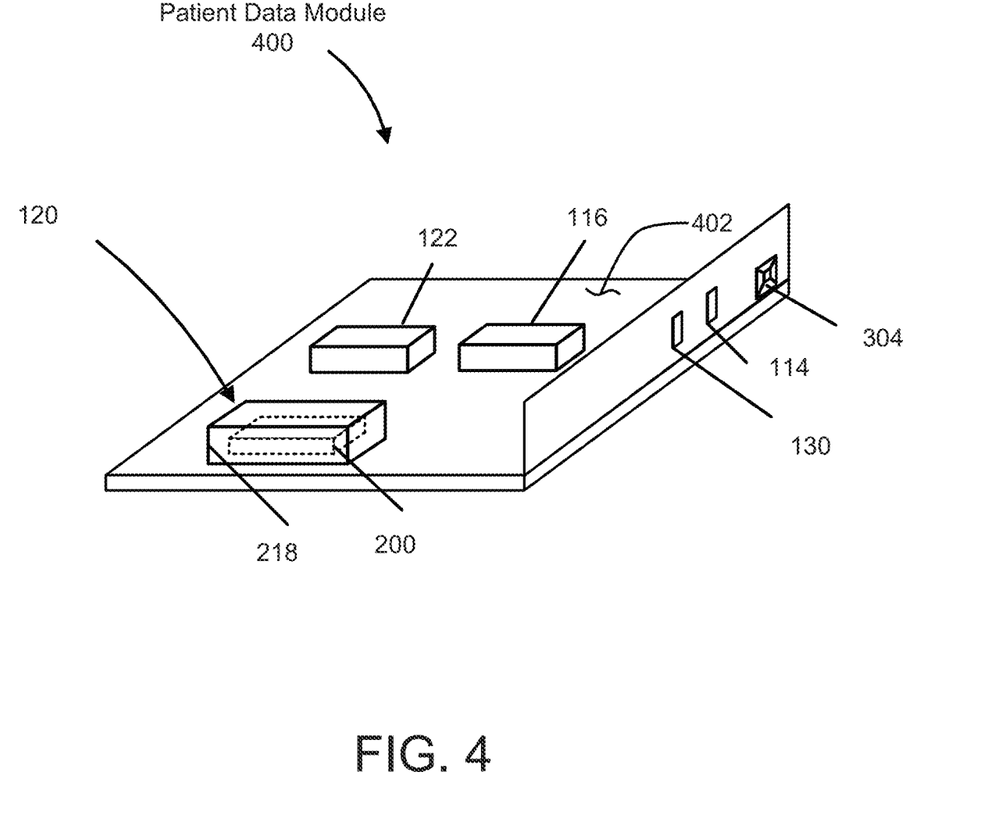
FIG. 4 is a block diagram illustrating a patient data module in accordance with an example of the present disclosure.

FIG. 4 illustrates an example of a patient data module 400 that includes various components previously described. As shown, the patient data module 400 includes a substrate 402, the visual indicator 304, network connectors 114 and 130, the controller 116, the cryptographic component 120, and the data storage 122. The cryptographic component 120 includes the housing 218, the controller 200 and other components (not shown) of the cryptographic component 120. The patient data module 400 may be installed in a medical device to enable the medical device to act as a patient data hub as described herein.

Figure 5:
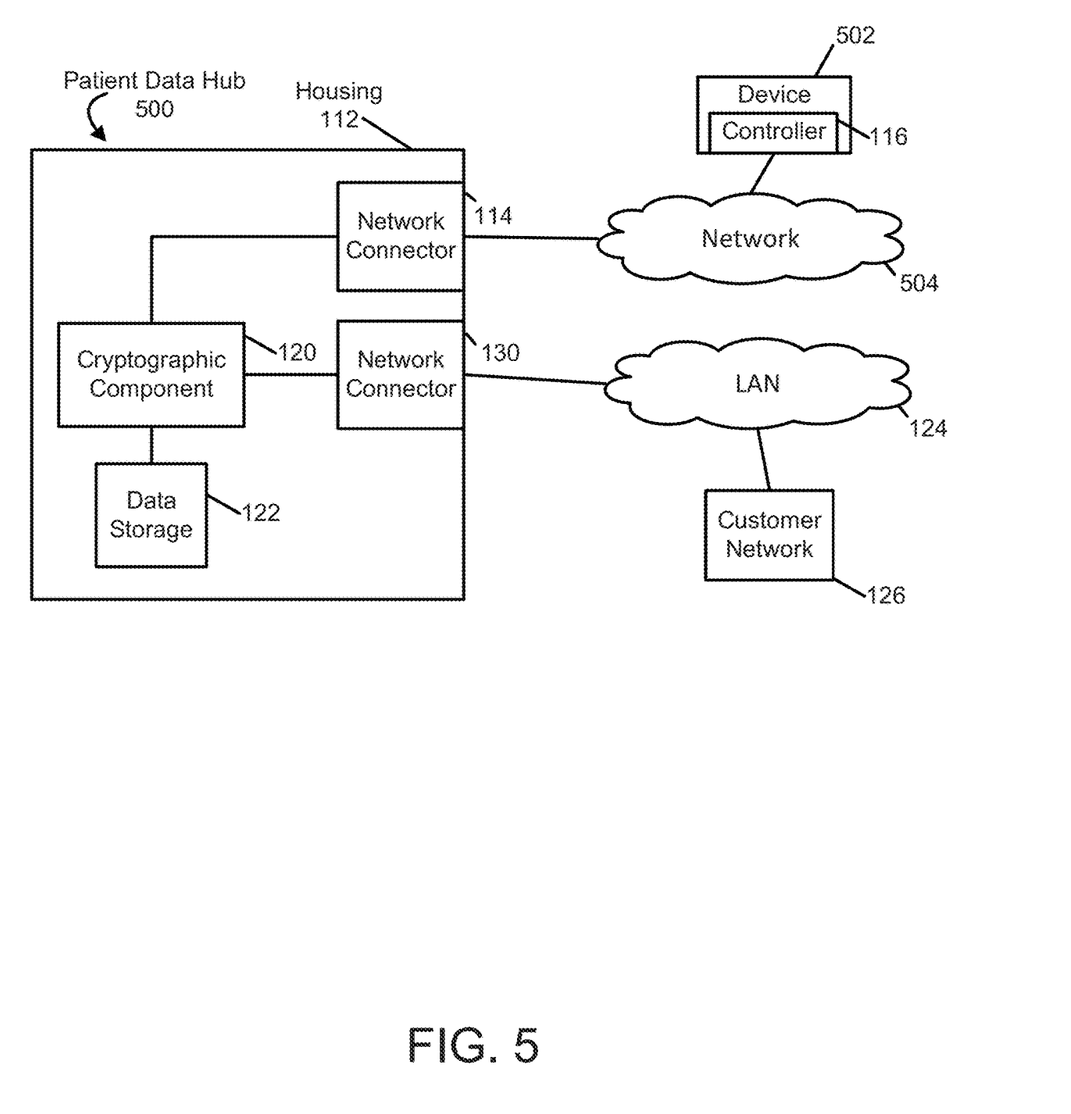
FIG. 5 is a block diagram illustrating another patient data hub within a hospital environment in accordance with an example of the present disclosure.

FIG. 5 illustrates another example of a patient data hub 500 that includes various components previously described within the context of a healthcare facility. As shown, FIG. 5 includes the patient data hub 500, a device 502, and a network 504. The patient data hub 500 includes the housing 112, network connectors 114 and 130, the cryptographic component 120, and the data storage 122. However, as shown in FIG. 5, the controller 116 is included in the device 502, which is separate and distinct from the patient data hub 500. In this example, the controller 116 communicates with the cryptographic component 120 via the network 504 and the network connector 114.

Figure 6:
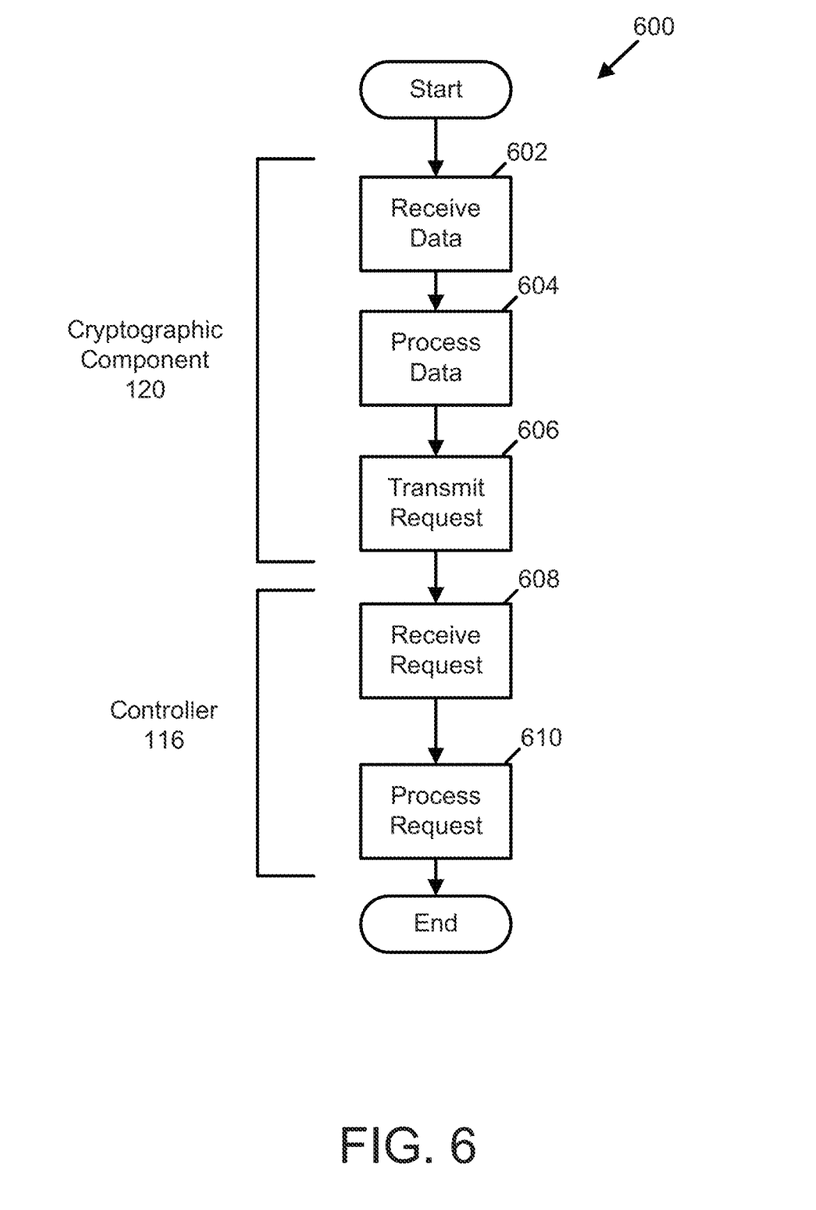
FIG. 6 is a flow diagram illustrating a secure configuration process in accordance with an example of the present disclosure.

FIG. 6 illustrates an example configuration process 600 executed by a patient data hub (e.g., the patient data hub 100) in accordance with some examples. As shown, the configuration process 600 starts in act 602 with a cryptographic component (e.g., the cryptographic component 120) of the patient data hub receiving configuration information. In some examples, the cryptographic component receives the configuration information via a physically or logically isolated port. The configuration information received by the cryptographic component may include, among other configuration information, CSPs, information descriptive of relationships between identifiers of operators, roles, and cryptographic services that the roles are authorized to execute, and information descriptive of data elements the cryptographic component is configured to receive from a controller (e.g., the controller 112), such as the information illustrated in Table 1.

In act 604, the cryptographic component processes the configuration information. This processing may include parsing the information to identify and store CSPs, information descriptive of operators, roles, and services, and information identifying one or more new shared security functions to be used to reformat inbound data prior to, or during, transmission of the inbound data from the controller to the cryptographic component.

In some examples, the parsing executed in the act 604 also identifies new device types and/or new data element types about which the cryptographic component may begin to receive information. In these examples, the cryptographic component configures itself to receive, process, and store data received from new devices and/or new data elements by storing configuration information descriptive of the new device types and/or new data element types. For example, a new model of wearable defibrillator with an added ability to acquire heart sounds may be introduced. To configure the patient data hub to process heart sounds data from the new model, the cryptographic component may receive, process, and store configuration information defining the new model type (e.g., wearable defibrillator, model 04-14-2011) and the new data element type (e.g., heart sounds data).

In some examples of the act 604, the cryptographic component prepares a configuration request for transmission to a controller (e.g., the controller 116) to configure the controller to use any new security functions and to handle any new device types and/or new data element types. The request may include configuration information descriptive of the one or more security functions, the new device types, and/or new data elements. In act 606, the cryptographic component transmits the request to the controller.

In act 608, the controller receives and parses the request. In act 610, the controller processes the request by updating its configuration information to reference the any new security functions and to include the new device types and/or new data types, and the configuration process 600 ends. Upon completion of this configuration update, the controller is configured to receive and process (e.g., using any new security functions) sensitive patient data including data originating from devices of the new device type and/or data being of the new data type.

Figure 7:
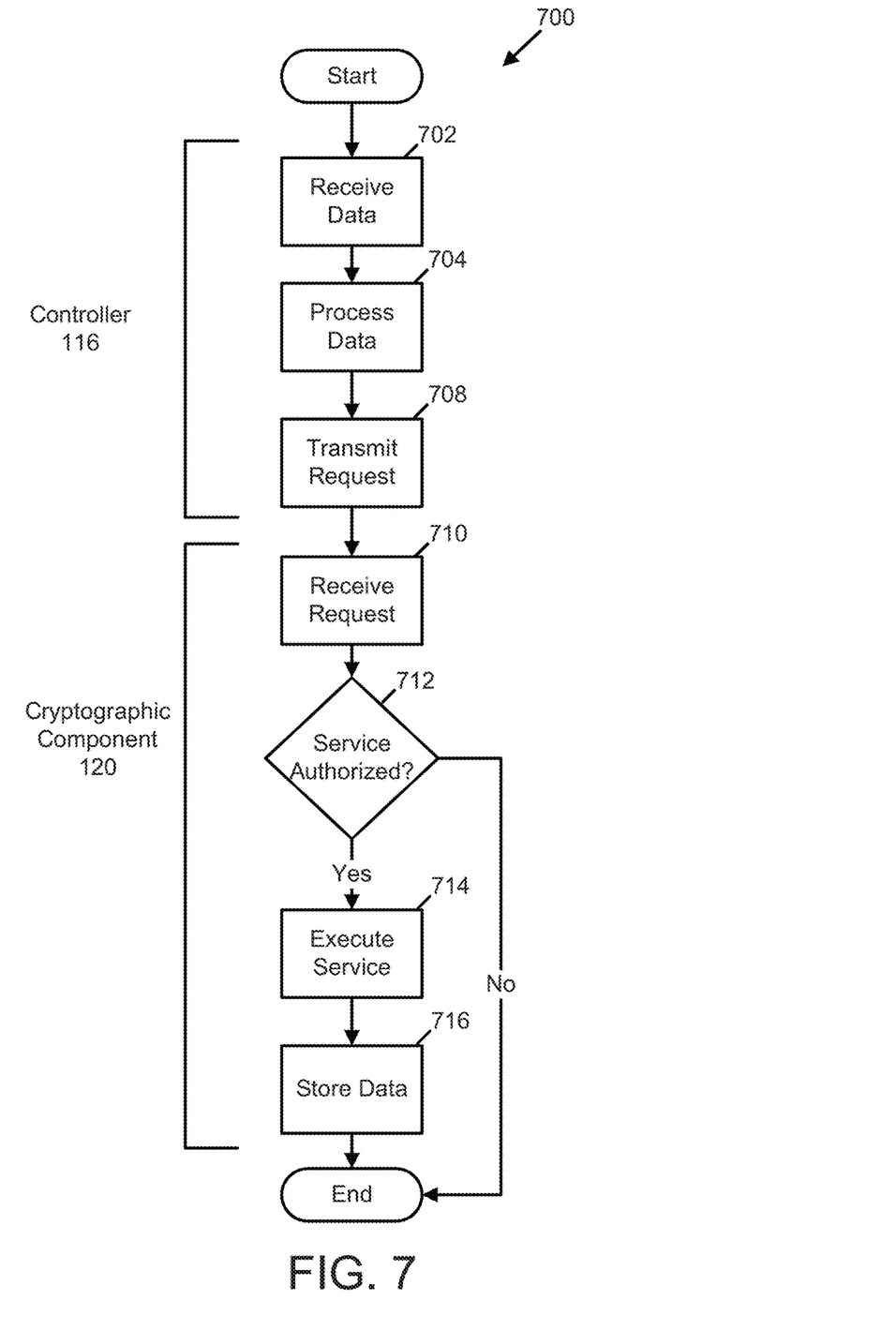
FIG. 7 is a flow diagram illustrating a data storage process in accordance with an example of the present disclosure.

FIG. 7 illustrates an example data storage process 700 executed by a patient data hub (e.g., the patient data hub 100) in accordance with some examples. As shown, the data storage process 700 starts in act 702 with a controller (e.g., the controller 116) of the patient data hub receiving inbound sensitive patient data. In some examples, the controller receives the inbound data from one or more medical devices that are not certified to any particular security or communication standard.

In some examples of the act 702, the controller filters inbound data to remove any unauthorized data elements. In these examples, the controller filters the inbound data by attempting to match each data element included in the inbound data a corresponding element of configuration information that specifies a data element the cryptographic processor is configured to process (e.g., the configuration information illustrated in Table 1). Where the controller identifies a match, the controller maintains the data element for subsequent processing. Where the controller does not find a match, the controller removes the data element from subsequent processing, records the presence of the authorized data, and/or issues a notification of the unauthorized data to an external device.

In act 704, the controller processes the inbound data. This processing may include parsing the inbound data to identify an operator of a device that originated the inbound data and reformatting the inbound data into a predefined format that a cryptographic component (e.g., the cryptographic component 120) is configured to receive and process. In some examples, this format may include a self-descriptive, extensible data format that is encrypted using a predefined security function. This security function may encrypt and/or compress the data.

In some examples of the act 704, the controller augments or modifies the inbound data. For instance, in one example, where the controller is unable to identify the operator of the originating device, the controller may generate and insert data identifying the operator as an operator associated with the patient data hub.

In another example, the controller parses the inbound data to identify and synchronize all chronological data elements included therein to a timeframe shared by the patient data hub and devices included in a customer network (e.g., the customer network 126). In this example, the controller parses the inbound data to determine an inbound timestamp marking the end of the transmission of the inbound data from the perspective of the transmitting device. The controller compares this inbound timestamp to a local timestamp generated by the patient data hub marking the end of the transmission of the inbound data from the perspective of the patient data hub. Next, the controller modifies at least some of the chronological data elements included in the inbound data to adjust for differences detected between the inbound timestamp and the local timestamp.

In act 708, the controller transmits a request for the cryptographic component to service the reformatted, inbound data. This service request may include the reformatted, inbound data, the identifier of the operator, and the identifier of the service. In act 710, the cryptographic component receives and parses the service request. This parsing process may include verifying that the service request is well-formed and includes inbound data reformatted in accord with one or more predefined security functions. This parsing process may further include decompressing and/or decrypting the reformatted, inbound data.

In act 712, the cryptographic component attempts to authenticate the identifier of the operator to a role and determines whether the role is authorized to request the service. If the identifier of the operator is authenticated to a role that is authorized to request the service, the cryptographic component executes the service in act 714, stores the serviced data in a data storage (e.g., the data storage 122) in act 716, and the data storage process 700 ends. If the identifier of the operator is not authenticated to a role that is authorized to request the service, the cryptographic component records the unauthorized request and/or issues a notification to an external device, and the data storage process 700 ends.

The processes disclosed herein each depict one particular sequence of acts in a particular example. The acts included in these processes may be performed by, or using, one or more patient data hubs or modules specially configured as discussed herein. Some acts are optional and, as such, may be omitted in accord with one or more examples. Additionally, the order of acts can be altered, or other acts can be added, without departing from the scope of the apparatus and methods discussed herein. Furthermore, as discussed above, in at least one example, the acts are performed on a particular, specially configured machine, namely a patient data hub or module configured according to the examples disclosed herein.

Having thus described several aspects of at least one example, it is to be appreciated that various alterations, modifications, and improvements will readily occur to those skilled in the art. For instance, examples disclosed herein may also be used in other contexts. In one such example, the patient data hub may be used to help integrate medical devices, as described in commonly owned U.S. Patent Application Ser. No. 62/315,486, titled SYSTEMS AND METHODS OF INTEGRATING AMBULATORY MEDICAL DEVICES, filed on Mar. 30, 2016, which is hereby incorporated herein by reference in its entirety. Such alterations, modifications, and improvements are intended to be part of this disclosure, and are intended to be within the scope of the examples discussed herein. Accordingly, the foregoing description and drawings are by way of example only.

The invention claimed is:

1. A patient data hub comprising:
   a housing;
   a first network interface disposed within the housing;
   a second network interface disposed within the housing and associated with a security standard for communication with one or more trusted devices;
   a first controller operably coupled to the first network interface;
   a second controller operably coupled to the second network interface and the first controller; and
   a tamper-evident device protecting the second controller,
   wherein the first controller is configured to
      receive sensitive patient data via the first network interface, and
      transmit the sensitive patient data to the second controller, and
   the second controller is configured to
      receive the sensitive patient data from the first controller,
      apply one or more security functions to secure the sensitive patient data according to the security standard associated with the second network interface to provide secured sensitive patient data,
      store the secured sensitive patient data in a data storage device,
      upon receiving a request for at least a portion of the secured sensitive patient data from a trusted device operably connected to the second network interface, provide the at least a portion of the secured sensitive patient data to the trusted device, and
authenticate an operator within a role prior to allowing the operator to execute any of a plurality of services associated with the role.

2. The patient data hub of claim 1, wherein the tamper-evident device comprises at least one of a coat and a seal.

3. The patient data hub of claim 1, further comprising an isolated interface and a security device protecting the second controller, wherein the security device is configured to zeroize critical security parameters in response detecting tampering and the second controller is configured to:
authenticate an operator's identity prior to allowing the operator to execute any of a plurality of services associated with the operator; and
allow external access to plaintext critical security parameters only through the isolated interface.

4. The patient data hub of claim 3, wherein the security device surrounds the second controller and the second controller is configured to zeroize all critical security parameters in response to detecting transgression of one or more threshold values by one or more environmental conditions.

5. The patient data hub of claim 4, wherein the one or more environmental conditions comprise current supplied to the second controller and a temperature of the second controller.

6. The patient data hub of claim 5, further comprising the data storage device, wherein the data storage device is surrounded by the security device.

7. The patient data hub of claim 1, wherein the security standard is compliant with at least one Federal Information Processing Standard security level.

8. The patient data hub of claim 1, wherein the first controller is configured to synchronize chronological data elements of the sensitive patient data with reference to a time identified by the first controller.

9. The patient data hub of claim 1, wherein the second controller is configured to receive configuration information, store the configuration information, and transmit the configuration information to the first controller.

10. The patient data hub of claim 9, wherein the configuration information comprises information descriptive of at least one of a new device model, a new data type, and a new security function.

11. A hospital information system comprising:
at least one medical device;
a trusted device; and
a patient data hub comprising
a housing,
a first network interface disposed within the housing and configured to be operably connected with the at least one medical device,
a second network interface disposed within the housing and associated with a security standard for communication with one or more trusted devices, the second network interface configured to be operably connected with the trusted device,
a first controller operably coupled to the first network interface,
a second controller operably coupled to the second network interface and the first controller, and
a tamper-evident device protecting the second controller,
wherein the first controller is configured to
receive sensitive patient data via the first network interface, and
transmit the sensitive patient data to the second controller, and
the second controller is configured to
receive the sensitive patient data from the first controller,
apply one or more security functions to secure the sensitive patient data according to the security standard associated with the second network interface to provide secured sensitive patient data,
store the secured sensitive patient data in a data storage device,
upon receiving a request for at least a portion of the secured sensitive patient data from the trusted device, provide the at least a portion of the secured sensitive patient data to the trusted device, and
authenticate an operator within a role prior to allowing the operator to execute any of a plurality of services associated with the role.

12. The system of claim 11, wherein the security standard is compliant with at least one Federal Information Processing Standard security level.

13. The system of claim 11, wherein the first controller is configured to synchronize chronological data elements of the sensitive patient data with reference to a time identified by the first controller.

14. The system of claim 11, wherein the second controller is configured to receive configuration information, store the configuration information, and transmit the configuration information to the first controller.

15. The system of claim 14, wherein the configuration information comprises information descriptive of at least one of a new device model, a new data type, and a new security function.

16. A patient data module comprising:
a substrate;
a first network interface disposed upon the substrate;
a second network interface disposed upon the substrate and associated with a security standard for communication with one or more trusted devices;
a first controller operably coupled to the first network interface;
a second controller operably coupled to the second network interface and the first controller; and
a tamper-evident device protecting the second controller,
wherein the first controller is configured to
receive sensitive patient data via the first network interface, and
transmit the sensitive patient data to the second controller, and
the second controller is configured to
receive the sensitive patient data from the first controller,
apply one of more security functions to secure the sensitive patient data according to the security standard associated with the second network interface to provide secured sensitive patient data,
store the secured sensitive patient data in a data storage device,
upon receiving a request for at least a portion of the secured sensitive patient data from a trusted device operably connected to the second network interface, provide the at least a portion of the secured sensitive patient data to the trusted device, and
authenticate an operator within a role prior to allowing the operator to execute any of a plurality of services associated with the role.

17. The patient data module of claim 16, wherein the security standard is compliant with at least one Federal Information Processing Standard security level.

18. The patient data module of claim 16, wherein the first controller is configured to synchronize chronological data elements of the sensitive patient data with reference to a time identified by the first controller.

19. The patient data module of claim 16, wherein the second controller is configured to receive configuration information, store the configuration information, and transmit the configuration information to the first controller.

20. The patient data hub of claim 1, wherein the trusted device comprises at least one computing device certified as being compliant with the security standard.

21. The patient data hub of claim 1, wherein the second controller is configured to determine the one or more security functions to be applied to the sensitive patient data based upon the security standard associated with the second network interface.

* * * * *